United States Patent
Zaid et al.

(10) Patent No.: US 11,484,492 B2
(45) Date of Patent: *Nov. 1, 2022

(54) TOPICAL MEDICAMENTS

(71) Applicant: Ankh Life Sciences Limited, Dublin (IE)

(72) Inventors: Gene H. Zaid, Hutchinson, KS (US); Beth Ann Wolf, Hutchinson, KS (US); Robert Preston Moore, Great Bend, KS (US); Rachel Elizabeth Ropp, Hutchinson, KS (US)

(73) Assignee: Ankh Life Sciences Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/853,508

(22) Filed: Apr. 20, 2020

(65) Prior Publication Data

US 2020/0330372 A1  Oct. 22, 2020

Related U.S. Application Data

(63) Continuation of application No. 16/795,937, filed on Feb. 20, 2020, now abandoned.

(60) Provisional application No. 62/835,633, filed on Apr. 18, 2019.

(51) Int. Cl.
| | |
|---|---|
| *A61K 36/889* | (2006.01) |
| *A61K 9/00* | (2006.01) |
| *A61K 31/11* | (2006.01) |
| *A61K 47/06* | (2006.01) |
| *A61K 36/185* | (2006.01) |
| *A61K 36/9066* | (2006.01) |
| *A61K 31/575* | (2006.01) |
| *A61K 31/375* | (2006.01) |

(52) U.S. Cl.
CPC ............ *A61K 9/0014* (2013.01); *A61K 31/11* (2013.01); *A61K 31/375* (2013.01); *A61K 31/575* (2013.01); *A61K 36/185* (2013.01); *A61K 36/889* (2013.01); *A61K 36/9066* (2013.01); *A61K 47/06* (2013.01)

(58) Field of Classification Search
None
See application file for complete search history.

(56) References Cited

U.S. PATENT DOCUMENTS

| | | |
|---|---|---|
| 2017/0042865 A1 | 2/2017 | Zaid et al. |
| 2019/0262416 A1 | 8/2019 | Zaid et al. |

FOREIGN PATENT DOCUMENTS

CN  104922587  *  9/2015

OTHER PUBLICATIONS

Vishwakarma et al., Scientific Reports, pp. 1-13, 2018, 8:12163.*
Drug Development and delivery, 2013.*
What is Turmeric ?, 14 pages, 2017.*
Cole et al. BMC Complementary and Alternative Medicine (2015) 15:264.*
Topical, 2 pages, 2021.*
Sethi et al. Moisturizers: The Slipper Road. Indian J. Dermatol. May-Jun. 2016; 61(3): 279-287. Available online at https://www.ncbi.nlm.nih.gov/pmc/articles/PMC4885180/?report=printable.
International Search Report and Written Opinion in co-pending PCT/US2020/018967, filed Feb. 20, 2020.
"Moisturizer." Wikipedia, Feb. 6, 2017 [retrieved via the internet on Apr. 24, 2020 at https://en.wikipedia.org/wiki/Moisturizer] para 6.
"Vanillin." Wikipedia, 1992 [retrieved via the internet on Apr. 24, 2020 at https://en.wikipedia.org/wiki/Vanillin] first figure.
"Ointments: Preparation and Evaluation of Drug Release." The Pharmaceutics and Compounding Laboratory. UNC, Apr. 24, 2020 [retrieved via the internet on Apr. 24, 2020 at https://pharmlabs.unc.edu/labs/ointments/bases.htm] table.
"Arumacil" brochure; Hyatt Life Sciences; 2019.

* cited by examiner

*Primary Examiner* — Michael V Meller
(74) *Attorney, Agent, or Firm* — Hovey Williams LLP

(57) ABSTRACT

Topical medicaments for the treatment of mammalian skin are provided, which include an actives fraction and a carrier fraction; the actives fraction comprises individual amounts of turmeric, *Peganum harmala*, and *Arum palaestinum*. In other embodiments, the actives fraction includes additional ingredients, including Vitamin C, β-sitosterol, and vanillin compound(s). The medicaments are useful in the treatment of a wide variety of conditions.

10 Claims, No Drawings

TOPICAL MEDICAMENTS

CROSS-REFERENCE TO RELATED APPLICATION

This is a continuation of U.S. patent application Ser. No. 16/795,937 filed Feb. 20, 2020 and claims the benefit of U.S. Provisional Patent Application Ser. No. 62/835,633 filed Apr. 18, 2019, both of which are incorporated by reference herein in their entireties.

BACKGROUND OF THE INVENTION

Field of the Invention

The present invention relates to topical medicaments for application to mammalian skin which include an actives fraction and a carrier fraction. The actives fraction has individual quantities of turmeric, *Peganum harmala*, and *Arum palaestinum*. In other embodiments, the actives fraction may include additional ingredients, such as Vitamin C, β-sitosterol, and vanillin compound(s). The invention also provides methods of treatment of mammals by skin application of the topical medicaments.

Description of the Prior Art

A large number of topical medicaments for application to skin have been proposed in the past for treatment of skin conditions or drug delivery. Indeed, the number and type of these medicaments, produced literally over thousands of years, is almost infinite. Nonetheless, researchers are constantly developing new medicament formulations.

SUMMARY OF THE INVENTION

The present invention provides a new and effective class of topical medicaments broadly comprising an actives fraction and a carrier fraction, the actives fraction including individual amounts of turmeric, *Peganum harmala*, and *Arum palaestinum*. Generally, the turmeric ingredient is present in an amount greater than that of the *Peganum harmala* and *Arum palaestinum*. The carrier fraction includes a base and, in many instances, a moisturizer as well. The medicaments may be applied to mammalian skin in order to ameliorate or eliminate conditions such as rashes, eczema, and cold sores.

Usually, the actives fraction includes from about 35-70% by weight turmeric and from about 15-40% by weight each of *Peganum harmala* and *Arum palaestinum*, based upon the total weight of the actives fraction taken as 100% by weight. More preferably, the turmeric is present at a level of from about 40-60% by weight, and the *Peganum harmala* and *Arum palaestinum* each are present at a level of from about 18-32% by weight. The actives fraction is present at a level of from about 0.5-15% by weight, while the carrier fraction is present at a level of from about 85-99.5% by weight, all based upon the total weight of the medicament taken as 100% by weight.

The actives fraction may include other ingredients, such as individual amounts of Vitamin C, β-sitosterol, and vanillin compound(s). Typical six-component actives fractions include from about 10-25% by weight turmeric, from about 4-15% by weight each of *Peganum harmala* and *Arum palaestinum*, from about 5-18% by weight Vitamin C, from about 4-15% by weight β-sitosterol, and from about 35-60% by weight vanillin compound(s), based upon the total weight of the six-component actives fraction taken as 100% by weight. In these six-component formulations, the actives fraction is present at a level of from about 5-12% by weight, and the carrier fraction is present at a level of from about 88-95% by weight, based upon the total weight of the six-component actives fraction medicament taken as 100% by weight.

The base portion of the carrier fraction commonly includes a base selected from the group consisting of oleaginous, absorption-type, water-in-oil emulsion, oil-in-water emulsion, water-soluble and water-miscible bases, and mixtures thereof. Petrolatum is often most preferred, particularly where ointment preparations are desired. Where the carrier fraction also includes a moisturizer, those selected from the group consisting of emollients, humectants, occlusives, protein rejuvenators, and mixtures thereof are preferred.

The invention provides methods of treating mammals, including humans, for a variety of conditions. To this end, the medicaments of the invention may be in the form of ointments, unguents, salves, pastes, creams, gels, foams, emulsions, solutions, dispersions, drops, suppositories, powders, balms, unctions, pomades, rubs, embrocations, liniments, transdermal patches, and poultices.

DETAILED DESCRIPTION OF THE PREFERRED EMBODIMENT

Generally speaking, preferred topical medicaments in accordance with the invention comprise an actives fraction and a carrier fraction, and optional supplements. As further described below, the nature of the carrier fraction and the amount thereof largely determine the type of medicament which is formulated.

The Actives Fraction

The actives fraction includes, at a minimum, turmeric, *Peganum harmala*, and *Arum palaestinum*. In such three-component fractions, the amount of turmeric is greater than either of *Peganum harmala* or *Arum palaestinum*, e.g., the composition would typically include from about 35-70% by weight (more preferably from about 40-60% by weight) turmeric and from about 15-40% by weight (more preferably from about 18-32% by weight) each of *Peganum harmala* and *Arum palaestinum*, based upon the total weight of the three-component fractions taken as 100% by weight. In other embodiments, the actives fractions will include the aforementioned three ingredients, together with a number of different possible active ingredients. In one embodiment, β-sitosterol, Vitamin C, and one or more vanillin compounds are provided. Such six-component actives fraction would typically have from about 10-25% by weight (more preferably from about 12-20% by weight) turmeric, from about 4-15% by weight (more preferably from about 5-12% by weight) each of *Peganum harmala, Arum palaestinum*, and β-sitosterol, from about 5-18% by weight (more preferably from about 8-15% by weight) Vitamin C, and from about 35-60% by weight (more preferably from about 40-55% by weight) vanillin compound(s), again based upon the total weight of the six-component fraction taken as 100% by weight.

The vanillin compound(s) useful in the invention are phenyl aldehydes, and one family of such compounds have the structure

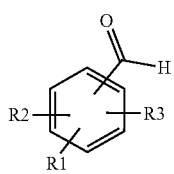

where R1 is selected from the group consisting of OH, H, C1-C4 alkoxy groups, F, Cl, Br, I, N, and NO2, and R2 and R3 are independently selected from the group consisting of H, OH, and C1-C4 alkoxy groups, it being understood that the aldehyde group and R1, R2, and R3 can be located at any position around the phenyl ring.

Certain specific vanillin compounds are vanillin, isovanillin, orthovanillin, and include the following exemplary vanillin compounds:

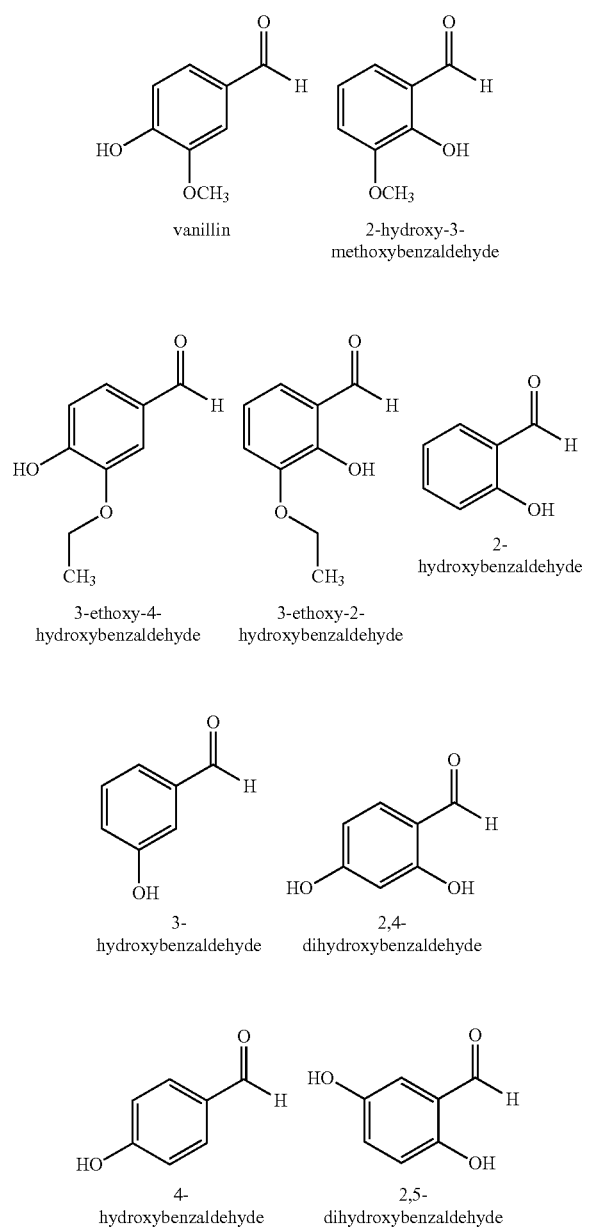

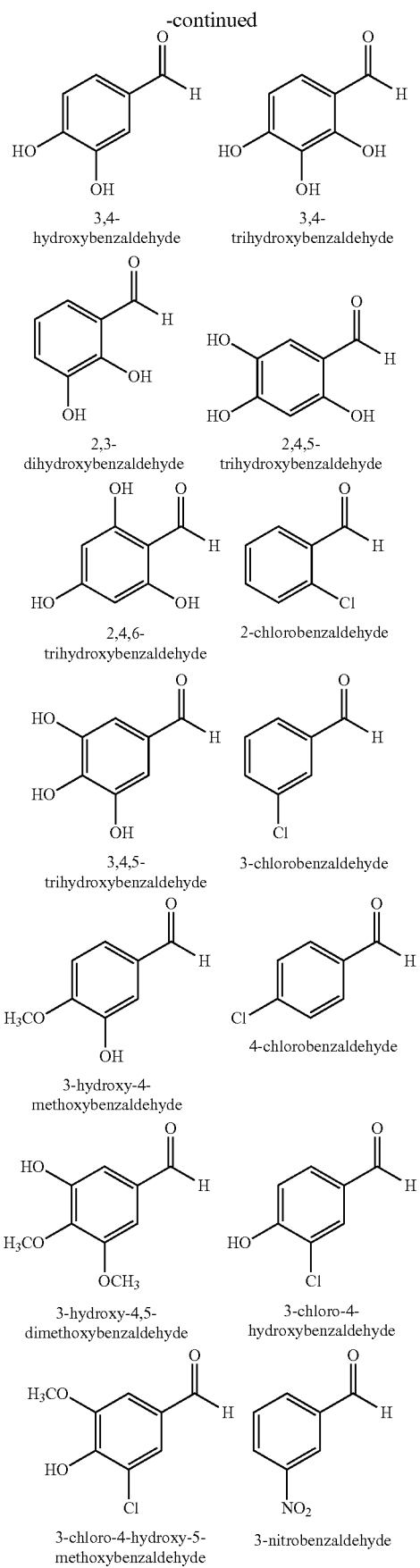

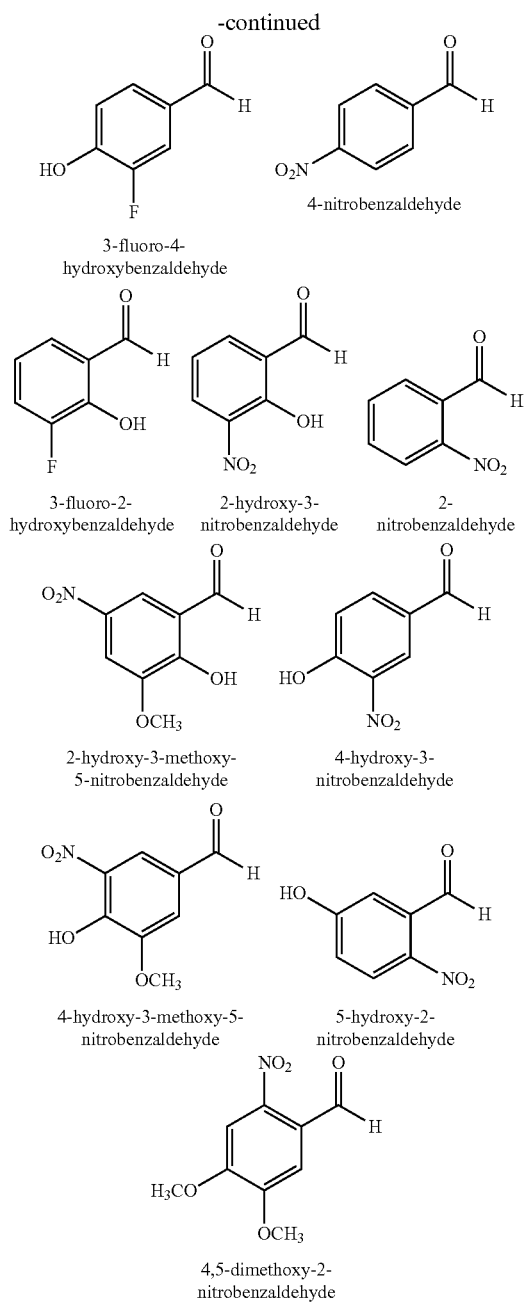

3-fluoro-4-hydroxybenzaldehyde 4-nitrobenzaldehyde 3-fluoro-2-hydroxybenzaldehyde 2-hydroxy-3-nitrobenzaldehyde 2-nitrobenzaldehyde 2-hydroxy-3-methoxy-5-nitrobenzaldehyde 4-hydroxy-3-nitrobenzaldehyde 4-hydroxy-3-methoxy-5-nitrobenzaldehyde 5-hydroxy-2-nitrobenzaldehyde 4,5-dimethoxy-2-nitrobenzaldehyde The Carrier Fraction Generally, the carrier fraction of the topical medicaments includes a base and, in most cases, a moisturizer. The base should be present at a level of from about 85-100% by weight (more preferably from about 85-99.5% by weight, and still more preferably from about 92-99% by weight), whereas the moisturizer when used is usually present at a level of from about 0.5-10% by weight (more preferably from about 1-4% by weight), based upon the total weight of the carrier fraction taken as 100% by weight.

The base may be selected from a broad number of different materials, depending upon the desired properties for the final topical medicaments, and may include a plurality of base ingredients. For example, and especially in the case of ointments, the base may be oleaginous (e.g., petrolatum or white ointment), absorption-type (e.g., hydrophilic petrolatum, anhydrous lanolin, Aquabase, Aquaphor, Polysorb), water-in-oil emulsions (e.g., hydrous lanolin, rose water, Eucerin, Nivea), oil-in-water emulsions (e.g., Dermabase, Delvachlol, Unibase), or water-soluble or water-miscible materials (e.g., polyethylene glycol, Polybase). Other base ingredients include alcohol tinctures (usually lower C1-C4 alcohols), Amlactin, cerave, coconut oil (both solid and liquid), essential oils, Fattibase, glycerine, lanolin, olive oil, propylene, sarna, soybean oil, sunflower oil, turmeric oil, water tinctures, zinc oxide, and mixtures thereof.

The moisturizer, when used, may be of virtually any type, such as emollients, humectants, occlusives, protein rejuvenators, and mixtures thereof.

Emollients are primarily liquids and oils, which serve to hydrate and improve skin softness, flexibility, and smoothness. Examples are cholesterol, squalene, fatty acids, fatty alcohols, and pseudo-ceramides. This category of moisturizers includes dry emollients (e.g., decyl oleate, isopropyl palmitate, isostearyl, alcohol), fatty emollients (e.g., castor oil, glyceryl stearate, jojoba oil, octyl stearate, propylene glycol), astringent emollients (e.g., cyclomethicone, dimethicone, isopropyl myristate, octyl octanoate), or protective emollients (e.g., dilinoleate, isopropyl isostearate).

Humectants are primarily hygroscopic compounds, and some may have emollient properties. Typical humectants are glycerin, alpha hydroxyl acids such as glycolic or lactic acid, sodium pyrrolidine carboxylic acid, propylene and butylene glycols, hyaluronic acid, urea, panthenol, aluminum and sodium lactates, gelatins, and sorbitol.

Occlusives create a hydrophobic barrier over skin and have the most pronounced effect when applied to slightly damaged skin. Exemplary occlusives include hydrocarbons (e.g., petrolatum, paraffin, mineral oil, caprylic/capric triglyceride, squalene), fatty acids (e.g., lanolin acid, stearic acid), fatty alcohols (e.g., cetyl alcohol, stearyl alcohol, lanolin), phospholipids (e.g., lecithin), polyhydric alcohols (e.g., propylene glycol), sterols (e.g., cholesterol), vegetable waxes (e.g., carnauba, candelilla), and wax esters (e.g., beeswax, lanolin, stearyl stearate).

Protein rejuvenators are normally small molecular weight proteins such as collagen, elastin, and keratin.

The Complete Topical Medicament Formulations

Considering first topical formulations containing the minimum three components of turmeric, *Peganum harmala*, and *Arum palaestinum*, the actives fraction would generally constitute from about 1.5-10% by weight (more preferably from about 1.8-5% by weight) of the complete formulation, whereas the carrier fraction would constitute the remainder, i.e., from about 90-98.5% by weight (more preferably from about 95-98.2% by weight), all of the foregoing percentages based upon the total weight of the complete formulations taken as 100% by weight. The minimum three-active formulations would have more turmeric than either of *Peganum harmala* or *Arum palaestinum*, and typically be in the ranges of from about 0.75-5% by weight (more preferably from about 0.6-4% by weight) turmeric, and from about 0.2-3% by weight (more preferably from about 0.05-1.5% by weight) each of *Peganum harmala* and *Arum palaestinum*, based upon the total weight of the three minimum component formulations taken as 100% by weight. The carrier fraction in each of these three-active formulations would constitute the balance, i.e., from about 90-98.5% by weight (more preferably from about 95-98.2% by weight).

The more preferred six-component formulations containing the minimum three components in addition to Vitamin C, β-sitosterol, and vanillin compound(s), would usually have from about 5-12% by weight actives fraction (more preferably from about 6-9% by weight), and correspondingly from about 88-95% by weight carrier fraction (more preferably from about 91-94% by weight), based upon the total weight of the six-component formulations taken as 100% by weight. The actives fraction would generally have from about 0.7-2% by weight turmeric (more preferably from about 0.9-1.8% by weight), from about 0.3-1% by weight each of *Peganum harmala* and *Arum palaestinum* (more preferably from about 0.5-0.8% by weight), from about 0.4-1% by weight Vitamin C (more preferably from about 0.6-0.9% by weight), 0.3-1% by weight β-sitosterol (more preferably from about 0.5-0.8% by weight), and from about 2-5% by weight vanillin compounds (more preferably from about 2.5-4% by weight), again based upon the total weight of the six-component formulations taken as 100% by weight.

The complete topical medicaments may be in a variety of forms, such as ointments, unguents, salves, pastes, creams, gels, foams, emulsions, solutions, dispersions, drops, suppositories, powders, balms, unctions, pomades, rubs, embrocations, liniments, transdermal patches, and poultices.

Other Optional Ingredients

Those skilled in the art will appreciate that the topical medicaments of the invention may include a variety of other optional ingredients, at the discretion of the formulator. For example, use can be made of pH modifiers, buffering agents, colorants, and aroma agents. These types of ingredients are typically used in very small amounts, such as 0.01-0.3% by weight, based upon the total weight of the topical medicament formulations taken as 100% by weight A preferred ointment product in accordance with the invention includes the following, for a 7500 mg batch: An actives fraction made up of 80 mg (1.07%) turmeric, 41 mg (0.55%) *Peganum harmala,* 40 mg (0.53%) *Arum palaestinum,* 40 mg (0.53%) β-sitosterol, 53 mg (0.71%) Vitamin C, and 206 mg (2.75%) vanillin; and a carrier fraction made up of 79.6 mg (1.06%) dimethicone, 6960.4 mg (92.8%) petrolatum. This ointment product was prepared by first heating the petrolatum to a temperature of about 60° C., followed by addition of the dimethicone and the remainder of the ingredients while mixing at a slow speed, avoiding cavitation. The product was then allowed to cool as a spreadable ointment.

This preferred ointment has been used by a number of individuals to ameliorate skin conditions.

An adult male suffered from severe rashes and/or eczema on his extremities. After seeing a dermatologist, he was prescribed and started on a compound containing Cetaphil and a steroid, which did not work. He then began administering the preferred ointment over a period of thirty days, with the result that his condition improved and his rashes and/or eczema were clearing. He also reported not having any subsequent flare-ups since he began using the ointment, and that his skin did not "tear or open up as easily as it did before." He is currently continuing to use the salve with positive results.

An adult male developed a cold sore on the left side of his upper lip. He began using the ointment and his condition stabilized and resolved within 48 hours. He also used the ointment on the entirety of his lips, not just the affected spot, because his cold sores usually spread after a breakout. The cold sore was contained to the initial spot and did not spread.

An adult male began using the ointment on his ears. He visited his dermatologist and, for the first time in 15 years, did not have to receive medical treatment for spots on his ears. He also reported that he used the ointment on a canker sore on the inner lining of his mouth and that the sore was completely resolved within two days. This same person reported using the ointment on his athlete's foot condition, which was resolved, along with small growths on his knee and forearm to good result.

An adult male was born with the cold sore virus and had experienced cold sores his entire life, approximately 3-4 times per month. Traditional over-the-counter treatments were used with no success. He began using the ointment over a period of two months and has experienced a reduction in the size and severity of cold sores, and a healing time of between 28 and 48 hours, which was a reduction by nearly a week of his reported standard healing time.

An adult female suffering from regular cold sore breakouts from a variety of stimuli began using the ointment over three months, and reported that healing time for each breakout had decreased. She also reported that use of the salve at the first sign of tingling had prevented a breakout on multiple occasions.

An adult male suffering from cold sores on a regular basis reported that when he first felt flare-ups, he applied the ointment to affected areas, resulting in clear-up within a day.

An adult male exhibited a skin lesion on his earlobe that had existed for many months. He began applying the salve on this lesion two to three times daily. Over a period of four to six weeks, the lesion gradually disappeared and then resolved completely. He then stopped using the ointment and the lesion came back. He restarted applying the salve and in several weeks' time, the lesion again disappeared. He has continued using the ointment and the lesion has not returned.

A pharmacist reported that he has seen several cases of shortened duration of cold sore episodes in his patients after application of the salve. He also has successful reports of treating acne and sunspots with the salve A woman was cooking and severely burned her hand. The injury was in the early stages of forming a blister when she applied the salve to be burn. The next morning, there was only a ½ inch red spot where the burn was and no pain at all. Over the next couple of days, the red mark completely resolved.

A woman reported that she had an outbreak of shingles that severely burned and itched. She applied the salve and, after five minutes, the burning and itching resolved and was gone.

A man had a canker sore on the inside of his lip that was causing severe pain. He applied the salve to the canker sore and the pain was "almost instantly gone."

A young man had a wart on his hand. The salve was applied over several weeks and the wart resolved and was gone.

There are three reports of teenagers using the salve on acne. The acne greatly improved over a number of days while these teenagers used the salve.

A woman developed a cold sore during an Alaskan cruise after being in the cold, windy conditions. She was unable to apply anything to the cold sore for 3 days and the cold sore aggressively progressed. She began using the salve and after one day of use, the cold sore became much less painful, raised, and aggravated. The cold sore resolved after four days of salve use.

A man reported he suffers from canker sores several times a year because of his acidic diet. He reported he woke up with a "huge canker sore on his lower front lip." He applied the salve that evening and when he woke up the next morning the canker sore was gone.

A young woman who was a college basketball player had terrible blisters on her feet. She applied the salve to the blisters several times daily and over the next week her blisters got steadily better.

A man suffered with chronic athlete's foot for most of his adult life. He applied the salve to his athlete's foot and in a day or two the athlete's foot cleared up and was gone.

A number of different topical medicament formulations were prepared for evaluation purposes. In each case, 1 g (w/w) of the six-component actives fraction described above was mixed with 15 g (w/w) of various carrier fractions listed below. Where solid carrier materials were employed, these were heated as described above in the preparation of the preferred ointment product, followed by addition of the actives fraction. In instances where the carrier was a liquid, the actives were simply mixed with the liquid. The carrier fractions tested in this manner were: alcohol tinctures, both ethanol and isopropyl; Amlactin; Aquaphor; cerave; cocoa butter; coconut oil, both solid and liquid forms; Dermabase; essential oils; Eucerin; Fattibase; glycerine; lanolin; olive oil; polyethylene glycol; Polybase; propylene; sarna; shea butter; soybean oil; sunflower oil; turmeric oil; Vitamin E oil; water tinctures; and zinc oxide.

We claim:

1. An emulsified topical medicament comprising a mixture of turmeric, *Peganum harmala*, and *Arum palaestinum* in a carrier fraction, wherein said turmeric is present in an amount greater than either of the amounts of the *Peganum harmala* or the *Arum palaestinum*.

2. The emulsified topical medicament of claim 1, said medicament is selected from the group consisting of ointments, unguents, salves, pastes, creams, gels, foams, emulsions, balms, pomades, rubs, transdermal patches, and poultices.

3. The emulsified topical medicament of claim 1, said turmeric being present at a level of from about 40-60% by weight, and said *Peganum harmala* and *Arum palaestinum* each being present at a level of from about 18-32% by weight, based upon the total weight of said turmeric, *Peganum harmala*, and *Arum palaestinum* taken as 100% by weight.

4. The emulsified topical medicament of claim 1, said medicament further comprising individual amounts of Vitamin C, β-sitosterol, and vanillin compound(s).

5. The emulsified topical medicament of claim 4, comprising:
said turmeric at a level of from about 10-25% by weight,
said *Peganum harmala* at a level of from about 4-15% by weight,
said *Arum palaestinum* at a level of from about 4-15% by weight,
said Vitamin C at a level of from about 5-18% by weight,
said β-sitosterol at a level of from about 4-15% by weight, and
said vanillin compound(s) at a level of from about 35-60% by weight, based upon the total weight of said turmeric, *Peganum harmala*, *Arum palaestinum*, Vitamin C, β-sitosterol, and vanillin compound(s) taken as 100% by weight.

6. The emulsified topical medicament of claim 1, said carrier fraction comprising petrolatum.

7. The emulsified topical medicament of claim 1, said carrier fraction comprising dimethicone.

8. The emulsified topical medicament of claim 1, said carrier fraction including a moisturizer.

9. The emulsified topical medicament of claim 8, said moisturizer is selected from the group consisting of emollients, humectants, occlusives, protein rejuvenators, and mixtures thereof.

10. The emulsified topical medicament of claim 1, including one or more vanillin compounds selected from the group consisting of compounds having the structure

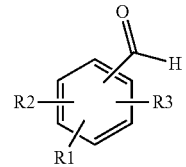

where R1 is selected from the group consisting of OH, H, C1-C4 alkoxy groups, F, Cl, Br, I, N, and NO2, and R2 and R3 are independently selected from the group consisting of H, OH, and C1-C4 alkoxy groups, it being understood that the aldehyde group and R1, R2, and R3 can be located at any position around the phenyl ring.

* * * * *